United States Patent [19]

Rees

[11] Patent Number: 4,816,488

[45] Date of Patent: Mar. 28, 1989

[54] METHOD OF TREATMENT

[75] Inventor: John A. Rees, Nottinghamshire, England

[73] Assignee: The Boots Company PLC, England

[21] Appl. No.: 159,542

[22] Filed: Feb. 23, 1988

[30] Foreign Application Priority Data

Feb. 28, 1987 [GB] United Kingdom ............... 8704777

[51] Int. Cl.$^4$ .......................................... A61K 31/135
[52] U.S. Cl. .................................................. 514/646
[58] Field of Search ........................................ 514/646

[56] References Cited

FOREIGN PATENT DOCUMENTS 0191542  8/1986  European Pat. Off. .
0230742  8/1987  European Pat. Off. .
2098602 11/1982  United Kingdom .

OTHER PUBLICATIONS

Lehrbuch Der Pharmakologie Und Toxikologie, ed H. Bader, 1982, Edition Medizin, pp. 125–127, 208 Weinheim, DE.
The Merck Index, 10th Ed. 1983, p. 1054, Merck & Co., Inc.

Primary Examiner—Stanley J. Friedman
Attorney, Agent, or Firm—Ostrolenk, Faber, Gerb & Soffen

[57] ABSTRACT

Compounds of formula I

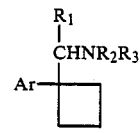

in which Ar is optionally substituted phenyl, $R_1$ is an optionally substituted aliphatic group and $R_2$ and $R_3$ are H or optionally substituted alkyl groups or $R_2$ and $R_3$ together with the nitrogen atom to which they are attached complete a heterocyclic ring, are used in the treatment of Parkinson's disease. The compounds of formula I may be administered with a dopamine precursor such as levodopa and/or a dopa decarboxylase inhibitor such as carbidopa or benserazide. A preferred compound of formula I is N,N-dimethyl-1-[1-(4-chlorophenyl)-cyclobutyl]-3-methylbutylamine hydrochloride monohydrate.

2 Claims, No Drawings

METHOD OF TREATMENT

This invention relates to the medical treatment of Parkinson's disease which is due to degenerative changes in the ganglia at the base of the cerebrum.

According to the present invention, there is provided a method of treating Parkinson's disease in which a therapeutically effective amount of a compound of formula I

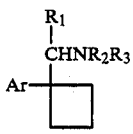

in which Ar is an optionally substituted phenyl, $R_1$ is an optionally substituted aliphatic group or a carbocyclic or heterocyclic group and $R_2$ and $R_3$ are H or optionally substituted alkyl groups or $R_2$ and $R_3$ together with the nitrogen atom to which they are attached complete a heterocyclic ring is administered in conjunction with a pharmaceutically acceptable diluent or carrier. The compound of formula I may be administered with a dopamine precursor such as levodopa and/or a dopa decarboxylase inhibitor such as carbidopa or benserazide.

Suitable compounds of formula 1 are described in British Pat. Nos. 2098602, 2127819 and 2128991 and in European patent application No. 191542 and may be used in the forms of pharmaceutically acceptable salts and in the form of solvates. A particularly preferred compound of formula I is N,N-dimethyl-1-[1-(4-chlorophenyl)cyclobutyl]-3-methylbutylamine hydrochloride monohydrate which is described in European patent application No. 230742.

Compounds of formula I which cause an increase in dopamine function have utility in the treatment of Parkinson's disease. N,N-Dimethyl-1-[1-(4-chlorophenyl)cyclobutyl]-3-methylbutylamine hydrochloride monohydrate is an inhibitor of dopamine reuptake and when administered to humans gives an increase in dopamine levels in plasma. It may be used alone in the treatment of Parkinson's disease or may be used in combination with a dopamine precursor such as levodopa and/or a dopa decarboxylase inhibitor such as carbidopa or benserazide.

Compounds of formula I may be administered in any of the known pharmaceutical dosage forms for example solid dosage forms such as tablets or capsules or liquid dosage forms for example those forms intended for oral or parenteral administration. The amount of the compound of formula I to be administered will depend on a number of factors including the age of the patient, the severity of the condition and the past medical history of the patient and always lies within the sound discretion of the administering physician but it is generally envisaged that the dosage of the compound of formula I to be administered will be in the range 1 to 1000 mg preferably 5 to 500 mg per day given in one or more doses. When the compound of formula I is administered with levodopa, the amount of levodopa given will be progressively increased by the physician until an optimum response is obtained. The actual amount will be under the control of the physician and may be up to 8 g per day given in divided doses. When the compound of formula I is administered with carbidopa, the amount of carbidopa given will be up to 100 mg per day. When the compound of formula I is administered with benserazaide, the amount of benserazide given will be up to 200 mg per day.

The ability of the compound to inhibit reuptake of dopamine is demonstrated by the following techniques.

(1) In vitro inhibition of dopamine uptake

Male Sprague-Dawley rats (Charles River) were killed by cervical dislocation and the brains removed and placed in an ice-cold oxygenated Krebs solution containing 120 mM NaCl, 4.7 mM KCl, 2.1 mM $KH_2PO_4$, 1.2 mM $CaCl_2$, 0.6 mM $MgSO_4$, 25 mM $NaHCO_3$ and 11 mM glucose. The brains were then dissected according to the method of Glowinski and Iversen [J. Neurochem. (1966) 13 655–669]and the striata removed. The samples of striata were pooled, weighed and transferred to a glass homogenising vessel on ice, containing oxygenated 0.32M sucrose solution (20 volumes). The striata were homogenised with six strokes of a ptfe pestle having a clearance of 0.35 mm (manufactured by TRI-R Homogenisers Ltd.). The homogenate was centrifuged at $1000 \times g$ for 10 minutes at 4° C. and the supernatant containing a suspension of synaptosomes was used in the dopamine uptake inhibition tests described below. Polythene specimen tubes containing 1.5 ml Krebs solution, 0.2 ml of a solution of N,N-dimethyl-1-[1-(4-chlorophenyl)cyclobutyl]-3methylbutylamine hydrochloride monohydrate or distilled water as control, and 0.1 ml of the synaptosome suspension were provided with an atmosphere of 5% carbon dioxide and 95% oxygen and pre-incubated at 37° C. for 5 minutes. A solution of $^{14}C$-dopamine hydrochloride (Amersham International) was added (0.Z ml) to give a final concentration of 0.17 $\mu M$. The incubation was continued for a further 5 minutes before the contents of the tubes were filtered under vacuum through Whatman GF/F filters which were washed with ice-cold Krebs solution (2×5 ml). The filters were placed in scintillation vials containing 10 ml scintillation fluid (ES-299 supplied by Packard Instruments) and the radioactivity in the vials counted on a Packard 4530 scintillation counter. In each experiment there was a control tube in which no test compound was present, 3 tubes in which the compound being tested was present at one of three concentrations (100, 10 and 1 $\mu M$) and a background tube containing no test compound which was maintained at 0° C. to determine passive $^{14}C$-dopamine uptake. The count for each tube was registered in counts per minute (cpm) and the % inhibition of uptake (I) calculated from the formula $$I = 100 \times \frac{\text{mean } cpm \text{ for control} - \text{mean } cpm \text{ for test}}{\text{mean } cpm \text{ for control} - \text{mean } cpm \text{ for background}}$$

The results obtained in three replicate experiments are set out below. The test compound inhibited $^{14}C$-dopamine uptake in a concentration-dependent manner. The concentration which gave 50% inhibition of uptake was then calculated and is given below as the IC50 figure for each experiment. The mean (±SEM) IC50 value for inhibition of dopamine uptake by the test compound is 11±4.2 $\mu M$.

| Concentration in Test Tube | % Inhibition of uptake | | |
|---|---|---|---|
| ($\mu M$) | Ex. 1 | Ex. 2 | Ex. 3 |
| 100 | 96 | 81 | 86 |

-continued

| Concentration in Test Tube | % Inhibition of uptake | | |
|---|---|---|---|
| (μM) | Ex. 1 | Ex. 2 | Ex. 3 |
| 10 | 70 | 35 | 48 |
| 1 | 31 | 4 | 12 |
| IC50 | 3.3 μM | 18 μM | 11 μM |

The results show that N,N-dimethyl-1-[1-(4-chlorophenyl)cyclobutyl]-3-methylbutylamine hydrochloride monohydrate inhibited the uptake of dopamine into striatal synaptosomes in vitro.

(2) In vivo inhibition of dopamine reuptake

An in vivo test for dopamine reuptake inhibition relies on the fact that such reuptake inhibitors can prevent the entry of dopamine-depleting agents into neurons. Depleting agents interfere with the neuronal storage mechanism for dopamine so dopamine leaks into the cytoplasm where it is metabolised by monoamine oxidase. Depleting agents therefore induce a large reduction in brain dopamine levels which can be measured experimentally. Prior treatment with a dopamine reuptake inhibitor reduces the depletion of dopamine levels caused by subsequent administration of a depleting agent such as α-methyl-m-tyrosine.

Male Sprague-Dawley rats (180–220 g; Charles River) were randomly assigned to various treatment groups. Two groups were dosed orally with vehicle (distilled water) and the remaining groups were given oral doses of N,N-dimethyl-1-[1-(4-chlorophenyl)cyclobutyl]-3-methylbutylamine hydrochloride monohydrate at 3 different doses. Thirty minutes later, one vehicle treated group and all the test groups were given an i.p. injection (2 ml/kg) of the depleting agent α-methyl-m-tyrosine (25 mg/kg; Sigma Chemical Co.). The group receiving vehicle (p.o.) plus α-methyl-m-tyrosine (i.p.) served as the depleted control. The remaining vehicle treated group was injected with saline i.p. to act as the absolute control.

Four hours after the i.p. injections, the animals were sacrificed and the whole brains rapidly removed and frozen on dry-ice. The samples were stored at −30° C. prior to determination of dopamine concentrations.

Brain samples were thawed and homogenised in 4 volumes of 0.4M perchloric acid containing sodium metabisulphite (0.4 mM) and the internal standard 3,4-dihydroxybenzylamine (0.8 μM). The samples were homogenised using a Polytron homogeniser on speed setting 6 for 10 seconds, after which they were centrifuged at 23,000×g for 10 minutes at 4° C. using a Sorvall RC-5B centrifuge and SM-24 rotor. Supernatants were removed and their dopamine concentration determined using an HPLC (high pressure liquid chromatography) system with fluorimetric detection.

The percentage prevention (P) of depletion of brain dopamine levels by test compounds is calculated from the formula $$P = 100 \times \frac{\text{Control} - \text{Test compound/depletor}}{\text{Control} - \text{deionised water/depletor}}$$

The test compound exhibited a dose-dependent prevention of brain dopamine depletion. From the percentage prevention values obtained at three doses an oral $ED_{50}$ dose was calculated, that is, the dose to prevent depletion of brain dopamine by 50%. The $ED_{50}$ for N,N-dimethyl-1-[1-(4-chlorophenyl)cyclo-butyl]-3-methylbutylamine hydrochloride monohydrate was calculated as 44 mg/kg (p.o.).

(3) Inhibition of dopamine uptake in vitro by plasma from drug treated rats

It has been demonstrated that the plasma of rats which have been treated with N,N-dimethyl-1-[1-(4-chlorophenyl)cyclobutyl]-3-methylbutylamine hydrochloride monohydrate inhibits the uptake of radiolabelled dopamine into freshly prepared synaptosomes from rat striatum.

To obtain the synaptosomes, untreated male CD rats (Sprague-Dawley 200–250 g; Charles River) were killed by cervical dislocation, the brains removed and the striata of two or three rats dissected out and placed in ice-cold saline. The pooled tissue was homogenised in 20 volumes of ice-cold 0.32M sucrose in a glass-teflon homogeniser with 0.35 mm clearance. The homogenate was spun at 1500×g for 10 minutes in a refrigerated (4° C.) Heraeus Christ minicentrifuge. The supernatant was transferred into a polypropylene sterilin tube and stored on ice for as short a time as possible prior to use in the radiolabelled dopamine uptake assay.

Male CD rats (Sprague-Dawley 350–400 g; Charles River) were given 10, 30 or 100 mg/kg of N,N-dimethyl-1-[1-(4-chlorophenyl)cyclobutyl]-3-methylbutylamine hydrochloride monohydrate which was dissolved in distilled water and administered orally at a rate of 5 ml/kg. Control rats were orally administered distilled water. After one hour the rats were killed by $CO_2$ inhalation overdose, the chest cavity opened and blood immediately removed from the heart and mixed with an anticoagulant solution.

The rat blood/anticoagulant mixture was spun at 5750×g for 20 minutes in a Heraeus Christ minicentrifuge at room temperature. The plasma was removed and kept at room temperature for as short a time as possible before analysis in the radiolabelled dopamine uptake assay. The fresh plasma samples from the rat study were initially maintained at 37° C. for 10–15 minutes before starting the assay. 300 μl of each plasma sample was added to six 5 ml polypropylene tubes already containing 50 μl of saline at room temperature. Four of these tubes were incubated at 37° C. to assess active radiolabelled dopamine uptake. The other two tubes were immediately cooled to c.3° C. and maintained at this temperature to account for passive radiolabelled dopamine uptake.

(a) Active uptake of radiolabelled dopamine

To each tube at 37° C. was added 100 μl of fresh striatal synaptosomes, prepared as above. These tubes were then agitated in the water bath at 37° C. for 5 minutes prior to the addition of 50 μl ice-cold $^3$H-dopamine solution (final concentration $1 \times 10^{-7}$M) (Amersham International). The reaction was stopped after a further 5 minutes of agitation and incubation at 37° C. by removing the tubes from the water bath and immediately adding 4 ml of ice-cold saline. The contents of the tube were then rapidly filtered over Whatman glass fibre (GF/F) filters supported on a Millipore 1225 manifold linked to an Edwards 2-stage vacuum pump. The tubes were rinsed with 2×4 ml of ice-cold saline and this was also rapidly filtered. Finally, each manifold well was washed with 4 ml of ice-cold saline.

(b) Passive uptake of radiolabelled dopamine

To the two tubes maintained at c.3° C. was added 100 μl of fresh striatal synaptosomes followed by 50 μl of ice-cold $^3$H-dopamine solution (final concentration $1\times 10^{-7}$M). The "reaction" in these tubes was terminated by the addition of 4 ml ice-cold saline and the samples were then rapidly filtered and washed as described in (a) above.

All filters were placed into glass vials and 10 ml of Packard ES-299 scintillation fluid added. Filters were allowed to solubilise for at least 1 hour before the radioactivity accumulated was assayed by liquid scintillation counting.

(c) Calculation of percentage inhibition of $^3$H-dopamine uptake

The amount of passive uptake of $^3$H-dopamine at c.3° C. (measured in cpm) was subtracted from the amount of active $^3$H-dopamine uptake at 37° C. (measured in cpm) to derive net $^3$H-dopamine uptake. The resulting value was then expressed as a percentage (X) of the net $^3$H-dopamine uptake recorded for control plasma. The latter plasma samples were obtained from distilled water-treated control rats. The percentage inhibition value (X) was calculated using the following formula:

$$X = 100 \times \frac{(\text{CONTROL } a - \text{CONTROL } p) - (\text{TREATED } a - \text{TREATED } p)}{(\text{CONTROL } a - \text{CONTROL } p)}$$

$a$ = active $p$ = passive

Mean [±1 standard error of the mean (SEM)] percentage inhibition was then determined for each dose.

The results obtained for 12 different rats (4 rats at each dose) are given below.

| Dose of Drug | % Inhibition of dopamine uptake in Individual Rats | | | | Mean (± SEM) |
|---|---|---|---|---|---|
| 100 | 53 | 59 | 67 | 55 | 58.5 ± 3.1 |
| 30 | 54 | 35 | 49 | 42 | 45.0 ± 4.1 |
| 10 | 33 | 23 | 13 | 17 | 22.8 ± 5.5 |

These results clearly show that plasma from rats administered N,N-dimethyl-1-[1-(4-chlorophenyl)cyclobutyl]-3-methylbutylamine hydrochloride monohydrate demonstrates a dose-dependent inhibition of radiolabelled dopamine uptake into rat striatal synaptosomes.

(4) Inhibition of dopamine uptake in vitro by plasma from drug treated rats obtained over a period of time after a single 30 mg/kg dose The percentage inhibition of dopamine uptake was determined in a similar manner to that described in (3) above. Plasma was obtained from different animals at various periods after oral administration of a dose of 30 mg/kg of N,N-dimethyl-1-[1-(4-chlorophenyl)cyclobutyl]-3-methylbutylamine hydrochloride monohydrate. The results obtained are set out below:

| Time after dosing (hrs) | % Inhibition of dopamine uptake - Mean (± SEM) |
|---|---|
| 1 | 45.0 ± 4.1 |
| 3 | 63.0 ± 1.7 |
| 8 | 73.4 ± 3.5 |
| 24 | 31.5 ± 2.4 |
| 48 | 19.5 ± 5.2 |
| 72 | 10.4 ± 1.6 |

These results show that the ability of rat plasma to inhibit the uptake of dopamine into synaptosomes from rat striata persists for a considerable period of time after dosing with drug.

(5) Inhibition of dopamine uptake in vitro by plasma from humans treated with drug It has been demonstrated that the plasma obtained from human volunteers administered N,N-dimethyl-1-[1-(4-chlorophenyl)cyclobutyl]-3-methylbutylamine hydrochloride monohydrate inhibits the uptake of radiolabelled dopamine into freshly prepared synaptosomes from rat striatum which were obtained as described in (3) above.

Venous blood (100 ml) was collected immediately before an oral 50 mg dose of N,N-dimethyl-1-[1-(4-chlorophenyl)cyclobutyl]-3-methylbutylamine hydrochloride monohydrate was administered to six healthy human volunteers and a further venous blood sample was taken 3 hours later. The plasma was separated by centrifugation at 2900×g for 20 minutes at room temperature in a Heraeus Christ minicentrifuge and was stored at −20° C. prior to analysis. The samples were thawed in a water bath at 37° C. for 10–15 minutes prior to commencement of the in vitro dopamine uptake assay which was performed as described in (3) above except $^{14}$C-dopamine was used. The assay was performed twice on plasma from each volunteer. The results obtained are given below:

| Volunteer | % Inhibition of dopamine uptake | | Mean |
|---|---|---|---|
| 1 | 21.6 | 1.5 | 11.6 |
| 2 | 15.5 | 1.6 | 8.6 |
| 3 | 13.4 | 17.9 | 15.7 |
| 4 | 9.2 | 26.6 | 17.9 |
| 5 | 13.0 | 18.4 | 15.7 |
| 6 | 9.9 | 22.3 | 16.1 |

The mean (±SEM) % inhibition of $^{14}$C-dopamine uptake by plasma from the six drug-treated volunteers was 14.2±1.4.

(6) Dopamine reuptake inhibition demonstrated by ipsilateral circling behaviour of unilateral nigrostriatal lesioned rats following drug administration The two tracts of the nigrostriatal dopamine system are independent and are located on either side of the midline of the brain. When one tract is destroyed using the specific neurotoxin, 6-hydroxydopamine (6-OHDA), rats will display characteristic circling behaviour after injection of dopaminergic drugs. The direction of rotation, however, is dependent on the stimulus employed. Drugs which inhibit dopamine reuptake can only function on the unlesioned side of the brain and induce circling towards the lesion site (known as ipsilateral circling.)

Male CD rats (250–300 g; Charles River) were anaesthetised with 'Equithesin' type anaesthetic (3.2 ml/kg i.p.) and secured in a stereotaxic frame (David Kopf Small Animal Stereotaxic Instrument DKI 900). After shaving the area, a saggital incision of 1.5–2 cm was made and skin flaps dissected from the skull. A small hole was made in the skull, using a No. 6 dental burr, to allow the tip of a 30 s.w.g. stainless steel cannula to be inserted to the left substantia nigra. This was located by using the following co-ordinates, using skull landmark bregma as the zero reference point; rostral-caudal −2.8; medial-lateral +2.0; dorsal-ventral −8.0 from the surface of the dura, all co-ordinates measured in millimetres. This system of co-ordinates is a modification of the de Groot system as described by Pellegrino et al (A stereotaxic atlas of the rat brain, 2nd Edition, Plenum Press 1979). 6-Hydroxydopamine HBr (2 $\mu g/\mu l$, as base; Sigma Chemical Co.) was injected into the left substantia nigra at 1 $\mu l$/min; a total of 8 $\mu g$ was administered over a period of 4 minutes using an infusion pump (Braun 'Perfusor' ED2). After removal of the cannula, the skin flaps were joined with a single everted suture and the animal allowed to recover.

After 21 days, the circling behaviour of the rats was examined. They were placed, individually, in circular plastic arenas (30 cm diameter × 12 cm high) for 1 hour, with no access to food or water during this period. Every 10 minutes each animal was observed for 1 minute and the number of 'turns' counted. One 'turn' consisted of rotation through 360° in either direction. As rats were always lesioned on the left side of the brain, anticlockwise turns were ipsilateral.

Control values were determined for all rats by observing their spontaneous circling behaviour in the arenas without prior dosing. The mean turns per minute was always less than 1.

The rats were challenged with an intraperitoneal dose of methamphetamine (2 mg/kg) and immediately placed in the arenas. In these experiments circling behaviour was monitored during two periods, 0–1h and 4–5h after dosing. Rats giving a mean of more than 5 ipsilateral turns per minute during the first hour in response to methamphetamine were used in subsequent tests. Following selection, the rats were used in groups of 5 or more rats to test the drug under investigation. The groups were made up of rats exhibiting varying responses to methamphetamine (always >5 turns/min as stated above), the mean response of the group was always more than 10 ipsilateral turns per minute.

N,N-Dimethyl-1-[1-(4-chlorophenyl)cyclobutyl]-3-methylbutylamine hydrochloride monohydrate was administered at 30 mg/kg orally and the amount of circling observed at various time periods after dosing is set out below:

| time (hrs) | ipsilateral turns/min (Mean ± SEM) |
| --- | --- |
| 0–1 | 3.0 ± 0.6 |
| 4–5 | 6.7 ± 1.4 |
| 8–9 | 8.6 ± 1.8 |
| 24–25 | 6.2 ± 1.7 |
| 48–49 | 1.7 ± 0.5 |

These results indicate that at this dose N,N-dimethyl-1-[1-(4-chlorophenyl)cyclobutyl]-3-methylbutylamine hydrochloride monohydrate has a long lasting action as an inhibitor of dopamine reuptake.

(7) Measurement of the turnover of dopamine in rodent brains by determination of DOPAC concentrations following drug administration Inhibition of dopamine reuptake in the brain reduces the rate at which dopamine is synthesised and metabolised (the turnover rate). This can be assessed by measuring the amount of the dopamine metabolite DOPAC (dihydroxyphenylacetic acid) which accumulates in the brains of rats and mice. In addition, the administration of probenecid blocks active transport of DOPAC out of the brain. The subsequent rise in brain DOPAC concentrations is attenuated by drugs which inhibit dopamine reuptake.

N,N-Dimethyl-1-[1-(4-chlorophenyl)cyclobutyl]-3-methylbutylamine hydrochloride monohydrate (10 mg/kg) was administered orally to male Sprague-Dawley rats (180–250 g) or male CD1 mice (25–30 g) (Charles River). One group of animals was killed two hours later. An additional group was administered probenecid (200 mg/kg i.p.; Sigma Chemical Co.) 30 minutes after the drug and then killed after a further 90 minutes. The animals were killed by decapitation and brains were rapidly removed and dissected on an ice-chilled porcelain plate. They were cut longitudinally along the midline; one half was retained for whole brain analysis while the striatum was dissected from the other. Tissues were immediately frozen in liquid $N_2$ and stored over dry ice (−80° C.) until assay. Whole brain tissue was homogenised in 5 volumes 0.4M perchloric acid (containing 0.01% (w/v) $Na_2S_2O_3$, 0.1% (w/v) EDTA) and striata in 600 $\mu l$ using a Polytron (setting 6; 20 seconds) fitted with a microprobe (PT-7). Samples were then centrifuged at 30,000×g (whole brain samples) or at 3,500×g (striata) using a microfuge (Beckman) set up to take 1200 $\mu l$ polypropylene tubes. Aliquots (50 $\mu l$) of the clear supernatants were then injected automatically into the chromatographic system for the separation and quantification of DOPAC.

High pressure liquid chromatography (HPLC) combined with electrochemical detection (ECD) was employed to assay DOPAC. A mobile phase (0.1M $Na_2HPO_4$: $CH_3OH$ (84:16%) containing 0.1% octanesulphonic acid, 0.1% EDTA and 0.01% $Na_2S_2O_3$) was delivered by a Dupont 870 pump module at a flow-rate of 1.0 ml/min to a reverse-phase analytical column (25×0.4 cm) and guard column (both packed with 5 pm Spherisorb ODS 2) maintained at 45° C. in a thermostatically controlled cabinet. Automatic sample injection was provided by a WISP 710B module (Waters Associates) and ECD was performed using a Bioanalytical Systems LC4A controller and cell, with a glassy carbon electrode maintained at 0.65 v versus a Ag-AgCl reference electrode. The controller was set at 20 nA full-scale and output from the cell recorded using a Spectra-Physics 4100 automatic computing integrator. Quantification of DOPAC was effected by the computing integrator after calibration of the HPLC-ECD system using DOPAC of known concentration and including isoprenaline as an internal standard.

The results obtained for the effect of the drug on brain DOPAC levels are set out below. Experiments marked A show the ability of drug alone to reduce brain DOPAC concentrations. Experiments marked B show the ability of the drug to attenuate the probenecid-induced elevation of brain DOPAC concentrations.

| Animal | Brain region | DOPAC Levels (ng/g wet wt) Control | Drug |
|---|---|---|---|
| A mouse | whole | 74 ± 5 | 54 ± 3 |
| A rat | whole | 62 ± 5 | 36 ± 4 |
| A rat | striatum | 921 ± 56 | 601 ± 17 |
| B mouse | whole | 116 ± 8 | 54 ± 3 |
| B rat | whole | 169 ± 3 | 130 ± 9 |
| B rat | striatum | 1325 ± 79 | 920 ± 70 |

The decreases in brain DOPAC concentrations are indicative of dopamine reuptake inhibition causing a decrease in dopamine turnover in drug treated animals.

The ability of N,N-dimethyl-1-[1-(4-chlorophenyl)-cyclobutyl]-3-methylbutylamine hydrochloride monohydrate to increase the dopamine level in the plasma of human subjects to which the compound had been administered was illustrated by the following trial.

The amount of dopamine in the plasma of six humans subjects who had received a single dose of 30 mg N,N-dimethyl-1-[1-(4-chlorophenyl)cyclobutyl]-3-methylbutylamine hydrochloride monohydrate per day for seven days was measured in plasma samples taken two hours after administration. The mean value of domamine in picograms/ml is set out below at days 1, 4 and 7. Eight human subjects who were given placebo tablets provides plasma samples from which the mean control dopamine levels given below were obtained.

| | Dopamine levels (pg/ml) | | |
|---|---|---|---|
| | Day 1 | Day 4 | Day 7 |
| Control | 122 | 110 | 118 |
| Treated | 254 | 294 | 219 |

These figures clearly show that the plasma dopamine levels had increased in the human subjects to which N,N-dimethyl-1-[1-(4-chlorophenyl)cyclobutyl]-3-methylbutylamine hydrochloride monohydrate at a dose of 30 mg had been administered.

I claim:

1. A method for the treatment of Parkinson's disease which comprises orally or parenterally administering to a human patient in need thereof a pharmaceutically effective amount of a compound of the formula

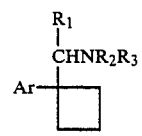

in which Ar is optionally substituted phenyl, $R_1$ is an optionally substituted aliphatic group and $R_2$ and $R_3$ are H or optionally substituted alkyl groups together with a pharmaceutically acceptable diluent or carrier.

2. A method as claimed in claim 1 wherein the compound is N,N-dimethyl-1-[1-(4-chlorophenyl)cyclobutyl]-3-methylbutylamine hydrochloride monohydrate.

* * * * *